United States Patent [19]

Sherman

[11] Patent Number: 5,954,925
[45] Date of Patent: Sep. 21, 1999

[54] METHOD AND APPARATUS FOR MANUFACTURING METHANOL

[75] Inventor: Jeffrey H. Sherman, Dallas, Tex.

[73] Assignee: GRT, Inc., Dallas, Tex.

[21] Appl. No.: 09/058,494

[22] Filed: Apr. 10, 1998

[51] Int. Cl.[6] .................................................. C07C 29/00
[52] U.S. Cl. ...................................................... 204/157.9
[58] Field of Search ......................... 204/157.9; 585/700

[56] References Cited

U.S. PATENT DOCUMENTS

| | | | |
|---|---|---|---|
| 3,773,659 | 11/1973 | Carlson et al. | 210/7 |
| 4,069,147 | 1/1978 | Abrams et al. | 210/6 |
| 4,132,637 | 1/1979 | Key et al. | 210/7 |
| 4,287,070 | 9/1981 | Pollock | 210/626 |
| 4,624,791 | 11/1986 | Ferriss | 210/704 |
| 4,861,471 | 8/1989 | Nakao et al. | 210/182 |
| 4,968,429 | 11/1990 | Yen | 210/637 |
| 5,137,607 | 8/1992 | Anderson et al. | 204/59 R |
| 5,156,173 | 10/1992 | Keyser et al. | 134/61 |
| 5,254,253 | 10/1993 | Behmann | 210/607 |
| 5,271,810 | 12/1993 | Keyser et al. | 202/185 |
| 5,316,682 | 5/1994 | Keyser et al. | 210/649 |
| 5,510,544 | 4/1996 | Keyser | 570/125 |
| 5,529,701 | 6/1996 | Grisham et al. | 210/787 |
| 5,531,904 | 7/1996 | Grisham et al. | 210/703 |
| 5,658,458 | 8/1997 | Keyser et al. | 210/195 |
| 5,662,811 | 9/1997 | Grisham et al. | 210/788 |

OTHER PUBLICATIONS

Article titled "Pplatinum Catalysts for the High–Yield Oxidation od Methane to a Methanol Derivative" by Roy A. Periana dated May 24, 1998 published in Science vol. 280.
Article titled Progress Report: Investigation of the Partial Oxidation of Methane to Methanol in a Simulated Countercurrent Moving Bed Reactor by the National Center For Environmental Research And Quality Assurance no date available.

Article titled "Photocatalytic Degradation of 2–Chlorophenol in TiO2 Aqueous Suspension: Modeling of Reaction Rate" by I. Rideh published 1997 in American Chemical Society no month available.
Article titled "Photocatalytic Degradation of Water Organic pollutants. Kinetic modeling and Energy Efficiency" by B. Serrano published 1997 in American Chemical Society no month available.
Article titled "Simplified Modeling of Radiant Fields in Heterogeneous Photoreactors.1.Case of Zero Reflectance" by Alberto Brucato published 1997 American Chemical Society no month available.
Article titled "Cylindrical Photocatalytic Reactors. Radiation Absorption and Scattering Effects Produced by Suspended Fine Particle in an Annular Space" by Roberto L. Romero published 1997 American Chemical Society no month available.
Article titled "Efficient photo–assisted Fenton catalysis mediated by Fe ions on Nafion membranes active in the abatement of non–biodegradable azo–dye" by Javier Fernandez published 1998 in Chemical Commun. no month available.

(List continued on next page.)

*Primary Examiner*—Kathryn Gorgos
*Assistant Examiner*—Edna Wong
*Attorney, Agent, or Firm*—Michael A. O'Neil

[57] ABSTRACT

In a method of and apparatus for manufacturing methanol from methane, a catalytic area is formed on the exterior of a hollow sintered stainless steel tube. Methane is maintained within the sintered stainless steel tube at predetermined pressure, and water continuously flowing across the exterior surface thereof strips the methane forming sub-micron sized methane bubbles. Ultraviolet light energy is directed onto the catalytic surface to form hydroxyl radicals from the flowing water. The hydroxyl radicals cleave the carbon-hydrogen bonds of the methane to form methyl ions which combine with the hydroxyl ions to form methanol.

1 Claim, 1 Drawing Sheet

OTHER PUBLICATIONS

Article titled "Kinetic Analysis of the Photocatalytic Degradation of Gas–Phase 2–propanol under Mass Transport–Limited Conditions with a TiO2 Film Photocatalyst" by Yoshihisa Ohko published 1998 in the J. Physi. Chem. no month available.

Article titled "Time–Dependent Behavior of Active Oxygen Species Formed on Photoirradiated TiO2 Films in Air" by Ken–ichi–Ishibashi published Mar. 19, 1998 in vol. 102, No. 12 of the Journal of Physical Chemistry B.

Article titled "Kinetics of Photocatalytic Reactions under extremely Low Intensity UV Illumination on Titanium Dioxide Thin Films" by Yoshihisa Ohko published 1997 J. Phys.Chem A. no month available.

Article titled "Preparation of a New Nanostructured TiO2 Surface Using a Two–Dimensional Array–Based Template" by Sachiko Matsushita published 1997 in The Chemical Society of Japan no month available.

Article titled "Electronic Structure of Discrete Pseudotetrahedral Oxovanadium Centers Dispersed in a Silica Xerogel Matrix: Implications for Catalysis and Photocatalysis" by Kim Tran published 1995 in American Chemical Journal no month available.

Article titled "Water Purification by Semiconductor Photocatalysis" by Andrew Mills published 1993 in Chemical Society Reviews no month available.

Article titled "Low–Temperature Nonoxidative Activation of Methane over H–Galloaluminsilicate (MFI) Zeolite" by Vasant R. Choudhary published Feb. 1997 by the American Association for the Advancement of Science.

Article titled "Semiconductor Photocatalysis" by Claire Jones found on the iternet at www.warwick.ac.uk/~msrjn/fsemic.html no date available.

Article titled "Factors Affecting Photocatalysis on Mesoporous Titanium Dioxide" by Victor Frank Stone, Jr. dated 1997 found on the internet at wwwl.che.ufl.edu/meeting/1997/annual/session/275/y/index.html no month available.

Article titled "Solar Chemical Process Engineering" found on the internet at http://chemengineer.tqn.com/library/weekly/aa063097.htm no date available.

Article titled "Titanium Dioxide Photocatalysis: Developing Remediation Technology for Multiple Wastes" By Tricia Drobat found on the internet at http://geology.wright.edu/geology/cgwm/iris/Waterline/page9.html no date available.

Article titled "Photochemical Treatment of Pollutants" found on the internet at http://www.nrel.gov/research/industrial tech/pollution.html no date available.

Article titled "Though a glass, not so darkly" found on the internet at http://ci.mond.org/9518/951811.html no date available.

Article titled "Green Technology for the 21st Century Photocatalysts" found on the internet at http://www.engr.wisc.edu/interd/wcp/Photocatalysts.html no date available.

Referenced cited at the USPTO found on the internet at http://patents.uspto.gov no date available.

METHOD AND APPARATUS FOR MANUFACTURING METHANOL

TECHNICAL FIELD

This invention relates generally to the manufacture of methanol, and more particularly to a method of and apparatus for manufacturing methanol from methane.

BACKGROUND AND SUMMARY OF THE INVENTION

Methanol, the simplest of the alcohols, is a highly desirable substance which is useful as a fuel, as a solvent, and as a feedstock in the manufacture of more complex hydrocarbons. In accordance with the method of methanol manufacture that is currently practiced in the petroleum industry, methane is first converted to synthesis gas, a mixture of carbon monoxide and hydrogen. The synthesis gas is then converted over an alumina based catalyst to methanol. The formation of synthesis gas from methane is an expensive process.

As will be apparent, methane and methanol are closely related chemically. Methane comprises a major component of a natural gas and is therefore readily available. Despite the advantages inherent in producing methanol directly from methane, no commercially valuable system for doing so has heretofore been developed.

The present invention comprises a method of and apparatus for manufacturing methanol which overcomes the foregoing and other deficiencies which have long since characterized the prior art. In accordance with the broader aspects of the invention there is generated a stream of sub-micron sized methane bubbles. Due to their extremely small size, the methane bubbles have an extremely large surface area which increases reaction efficiency. The methane bubbles are entrained in flowing water. Ultraviolet light energy interacting with a titanium-based catalyst forms hydroxyl radicals which cleave the carbon-hydrogen bonds in the methane to form methyl radicals. The methyl radicals combine with the hydroxyl radicals to form methanol.

In accordance with more specific aspects of the invention, a sintered stainless steel tube has an exterior coating comprising a titanium-based catalyst. The stainless steel tube is positioned within a glass tube, and water is caused to continuously flow through the annular space between the two tubes. Methane is directed into the interior of the sintered stainless steel tube and is maintained at a pressure just high enough to prevent the flow of water into the stainless steel tube. As the water passes over the stainless steel tube, methane bubbles are continually stripped off of the sintered surface. The methane bubbles thus generated are sub-micron in size and then therefore present an extremely large surface area.

Ultraviolet light energy generated from ultraviolet lamps is directed through the glass tube and engages the titanium-based catalyst to generate hydroxyl radicals in the flowing water. The hydroxyl radicals cleave the carbon-hydrogen bonds in the methane forming either molecules of hydrogen or molecules of water and methyl radicals. The methyl radicals combine with the hydroxyl radicals to form methanol. Subsequently, the methanol is separated from the water and the other products of the reaction by distillation.

BRIEF DESCRIPTION OF THE DRAWINGS

A more complete understanding of the invention may be had by reference to the following Detailed Description when taken in conjunction with the accompanying Drawings wherein.

DETAILED DESCRIPTION

Figure 1:
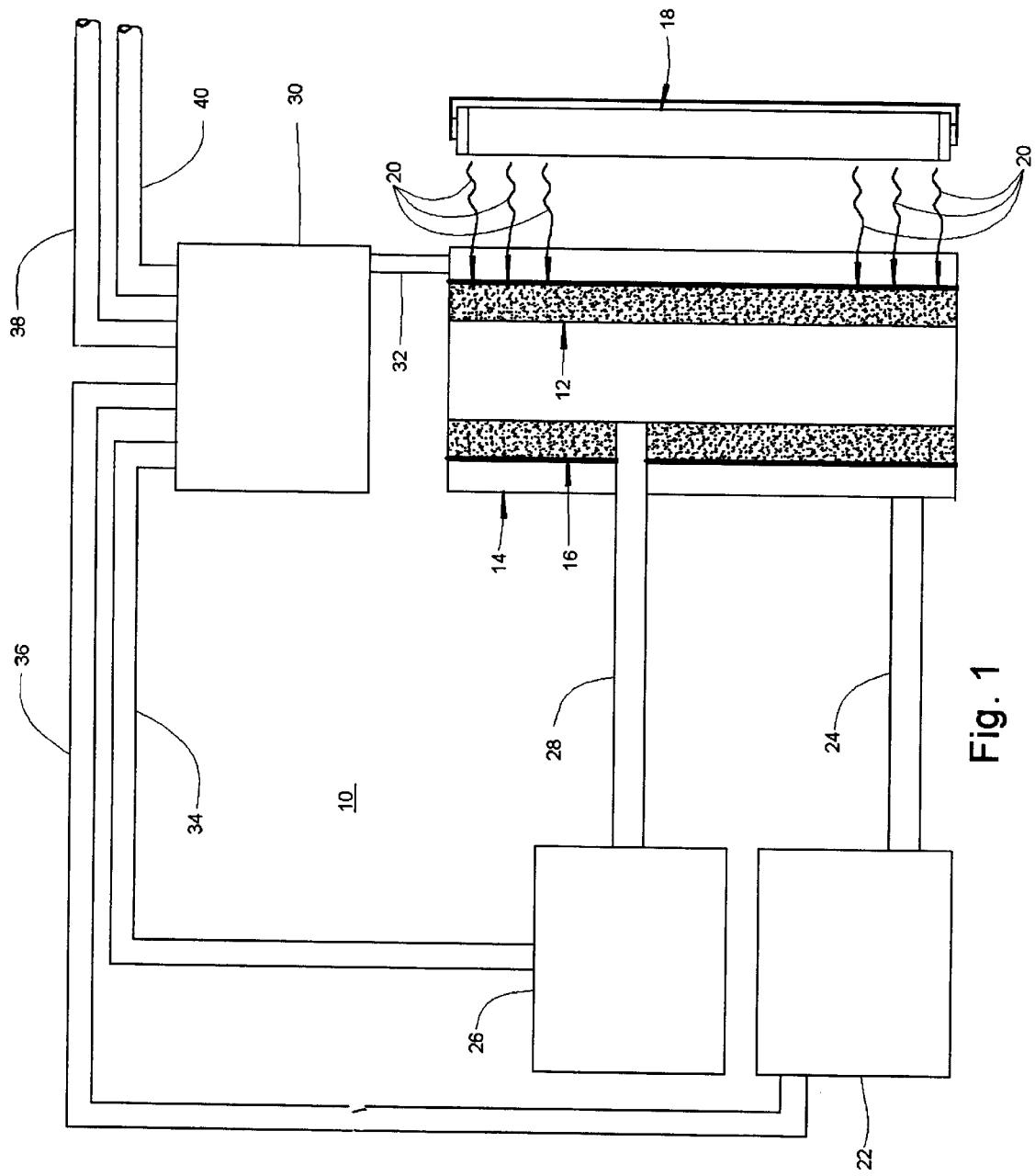
FIG. 1 is a diagrammatic illustration of the method and apparatus of the present invention.

Referring now to the Drawing, and particularly to FIG. 1 thereof, there is shown an apparatus for manufacturing methanol 10 comprising a preferred embodiment of the invention. The apparatus 10 includes a sintered stainless steel tube 12 positioned within a glass tube 14. As illustrated in FIG. 1, both the sintered stainless steel tube 12 and the glass tube 14 comprise right circular cylinders with the tube 12 extending concentrically relative to the tube 14. Other geometrical configurations of and positional relationships between the sintered stainless steel tube 12 and the glass tube 14 may be utilized in accordance with the requirements of particular applications of the invention.

The sintered stainless steel tube 12 has a catalyst layer 16 formed on the exterior surface thereof. The catalyst layer 16 is preferably a titanium-based catalyst; however, it will be understood that other catalyst types may be utilized in the practice of the invention, if desired. A plurality of ultraviolet lamps 18 are positioned around the exterior of the glass tube 14, it being understood that while only one lamp 18 as illustrated in FIG. 1, in actual practice a plurality of lamps 18 are employed and are disposed around the entire periphery of the tube 14. As illustrated by the waves 20 in FIG. 1, the ultraviolet lamps 18 generate energy in the form of ultraviolet light which is directed through the glass tube 14 and onto the catalytic layer 16 formed on the exterior surface of the sintered stainless steel tube 12.

In the operation of the apparatus for manufacturing methanol 10, a quantity of water is received in a reservoir 22. Water from the reservoir 22 is directed into the annular space between the sintered stainless steel tube 12 and the glass tube 14 through piping 24. During the operation of the apparatus 10, water flows through the annulus between the sintered stainless steel tube 12 and the glass tube 14 on a continuous basis.

A quantity of methane is stored in a reservoir 26. In the operation of the apparatus 10, methane is directed from the reservoir 26 into the interior of the sintered stainless steel tube 12 through piping 28. The pressure of the methane within the sintered stainless steel tube 12 is maintained just high enough to prevent the flow of water into the interior of the tube 12 through the sintered walls thereof In the operation of the apparatus for manufacturing methanol 10, the water flowing through the annular space between the sintered stainless steel tube 12 and the glass tube 14 causes methane bubbles to be continuously stripped off the sintered stainless steel surface of the tube 12. In this manner the size of the methane bubbles is maintained in the sub-micron range. The sub-micron size of the methane bubbles provides an enormous methane surface area which in turn results in unprecedented reaction efficiency.

As the sub-micron size methane bubbles are produced by the flow of water over the exterior surface of the sintered stainless steel tube 12, ultraviolet light energy from the lamps 18 continuously engages the catalytic surface 16 formed on the exterior of the tube 12. This generates hydroxyl radicals in the flowing water. The hydroxyl radicals homolyticaly cleave one or more of the carbon-hydrogen bonds in the methane thereby forming either molecules of hydrogen or molecules of water, depending upon the initiating radical, and methyl radicals. The methyl radicals combined either with the hydroxyl radicals to form methanol or with the hydrogen radicals to form methane.

Those skilled in the art will appreciate the fact that other chemical reactions are possible in the operation of the apparatus for manufacturing methanol 10. For example, there exists the possibility of a methyl-methyl radical reaction, and also the possibility of a hydrogen-hydrogen radical reaction. Both of these possibilities are extremely remote due to the relatively low concentrations of methyl radicals and hydrogen radicals at any given time.

The water flowing from the annulus from the sintered stainless steel tube 12 and the glass tube 14 having the reaction products contained therein are directed to a distillation apparatus 30 through piping 32. The distillation apparatus 30 separates the outflow from the space between the tube 12 and the tube 14 into at least four streams, including a stream of unreacted methane 34 which is returned to the reservoir 26, a stream of water 36 which is returned to the reservoir 22, a stream of other reaction products 38 which are recovered, and a stream of methanol 40. The stream of other reaction products 38 may be further separated into its component parts, if desired.

The present invention further comprises a method of making methanol. In accordance with the method there is provided a continuously flowing stream of water. Submicron size bubbles of methane are continuously injected into the flowing water. Hydroxyl radicals are continuously generated from the water. The hydroxyl radicals cleave the hydrogen-carbon bonds of the methane to form methyl radicals. The methyl radicals combined with the hydroxyl radicals to form methanol.

In accordance with more specific aspects of the method, a sintered stainless steel tube having a titanium-based catalytic layer on the exterior surface thereof is positioned within a glass tube. Water is directed through the annulus between the sintered stainless steel tube and the glass tube, and methane is directed into the interior of the sintered stainless steel tube. The water flowing between the sintered stainless steel tube and the glass tube continuously strips sub-micron sized bubbles from the exterior surface of the sintered stainless steel tube.

Ultraviolet light energy from ultraviolet lamps is directed through the glass tube and engages the catalytic surface on the exterior of the sintered stainless steel tube, thereby forming hydroxyl radicals from the flowing water. The hydroxyl radicals homolytically cleave one of the carbon-hydrogen bonds in the methane to form either molecules of hydrogen or molecules of water, and methyl radicals. The methyl radicals combine either with the hydroxyl radicals to form methanol or with the hydrogen radicals to form methane.

Although preferred embodiments of the invention have been illustrated in the accompanying Drawing and described in the foregoing Detailed Description, it will be understood that the invention is not limited to the embodiments disclosed but is capable of numerous rearrangements, modifications, and substitutions of parts and elements without departing from the spirit of the invention.

I claim:

1. A method for manufacturing methanol from methane comprising the steps of:

providing a hollow sintered stainless steel tube;

providing a layer of catalytic material on the exterior of the hollow sintered stainless steel tube;

maintaining a quantity of methane at predetermined pressure within the hollow sintered stainless steel tube;

continuously directing a flow of water across the exterior surface of the hollow sintered stainless steel tube; and continually directing ultraviolet light energy onto the catalytic surface on the exterior on the sintered stainless steel tube thereby forming hydroxyl ions from the flowing water;

the hydroxyl ions cleaving the carbon-hydrogen bonds of the methane to form methyl ions; and the methyl ions combining with the hydroxyl ions to form methanol.

\* \* \* \* \*